United States Patent [19]

Delest et al.

[11] Patent Number: 5,077,203
[45] Date of Patent: Dec. 31, 1991

[54] ENZYMATIC PROCESS FOR THE PREPARATION OF DEOXYKETOSES

[75] Inventors: Philippe Delest, Noisy-le-Roi; Colette Demuynck, St Amant-Tallende, both of France

[73] Assignee: Sanofi, Paris, France

[21] Appl. No.: 668,983

[22] Filed: Mar. 12, 1991

[30] Foreign Application Priority Data

Mar. 19, 1990 [FR] France ................................ 90 03469

[51] Int. Cl.$^5$ ............................ C12P 39/00; C12P 7/26
[52] U.S. Cl. ........................................ 435/42; 435/126; 435/148; 435/193
[58] Field of Search ................. 435/42, 148, 126, 193

[56] References Cited

U.S. PATENT DOCUMENTS

| | | | |
|---|---|---|---|
| 1,833,716 | 11/1931 | Kluyuer et al. | 435/148 |
| 4,250,259 | 2/1981 | Hou et al. | 435/148 |
| 4,696,897 | 9/1987 | Sonoyama et al. | 435/42 |

OTHER PUBLICATIONS

Chem. Abs. CA08:71633(9) Bolte et al., Tetrahedron Lett. (Teleay) vol. 28(45), pp. 5525-5528, 1987.

*Primary Examiner*—Herbert J. Lilling
*Attorney, Agent, or Firm*—Wegner, Cantor, Mueller & Player

[57] ABSTRACT

The invention relates to a process for the preparation of compounds of formula

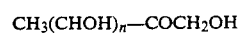

$$CH_3(CHOH)_n\text{—}COCH_2OH$$

in which n is an integer from 1 to 4, wherein L-serine, glyoxylic acid and an aldehyde of formula $CH_3(CHOH)_{n-1}CHO$ are reacted in the presence of a glyoxylate aminotransferase and a transketolase. The intermediate aldehyde $CH_3(CHOH)_2CHO$ is enzymatically prepared by the action of a polyol dehydrogenase and a xylose reductase on $CH_3CHOHCOCH_2OH$.

14 Claims, No Drawings

ENZYMATIC PROCESS FOR THE PREPARATION OF DEOXYKETOSES

The present invention relates to the enzymatic preparation of deoxyketoses.

Deoxyketoses, which are of the formula $$CH_3(CHOH)_nCOCH_2OH$$

in which n equals 1 to 4, are scarce in nature.

The food industry requires "natural" flavors for incorporating into various food products, given that a large number of consumers no longer want artificial additives. Consequently, it is necessary to develop processes for obtaining flavors which may be described as natural; such processes should require only natural raw materials, and this precludes the use of the usual reagents of organic chemistry. The industry has thus turned towards the use of enzymatic reactions involving microorganisms or enzymes, particularly of plant origin. The present invention enables natural products to be prepared which are flavor components or which may thereafter be converted into the latter.

Thus, for example, it is possible to prepare enzymatically by this process, using natural products, 6-deoxy-L-sorbose, one of the stereoisomers of 6-deoxy-2-hexulose, which is a precursor of Furaneol ®, a component of the caramel flavor, of formula

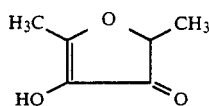

as described in J. Org. Chem. 48 p. 3493-3497 (1983).

The preparation of ketoses of formula

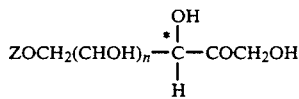

in which Z represents H or $PO_3H_2$ and n an integer from 0 to 3, by the action of an aldehyde of formula $$ZOCH_2-(CHOH)_{n-1}-CHO$$

on hydroxypyruvic acid in the presence of a transketolase has been described in Tetrahedron Letters 28 (45) p. 5525-5528 (1987).

Moreover, during studies of plant metabolism, reported in particular in the papers abstracted in Chem. Abs. 82 69722 x, 104 104540 h, 104 106363 b and 112 95532 t, the presence of aminotransferases in plants has been revealed as well as their participation in a transamination reaction between amino acids, particularly serine, glycine and alanine, and alpha-keto acids, particularly glyoxylic and pyruvic acids, a reversible reaction which results, in particular, in the formation of hydroxypyruvate and glycerate.

The applicants have now observed that transketolase substrates are not exclusively aldehydes bearing a hydroxyl group on each carbon of the chain, but that it is possible to obtain ketoses by reacting hydroxypyruvic acid with an aldehyde of formula $CH_3(CHOH)_nCHO$, with a low yield when n=0; in contrast, when hydroxypyruvic acid is produced in situ, by the action of L-serine and glyoxylic acid in the presence of glyoxylate transaminase, the yield of the reaction is higher, and the overall yield is substantially higher than that for the two reactions carried out successively.

The present invention therefore relates, according a first aspect, to a process for the preparation of a deoxyketose, a compound of formula

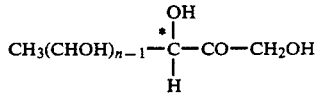

in which n is an integer from 1 to 4 and the carbon marked with an asterisk is in the S configuration, wherein L-serine, glyoxylic acid and an aldehyde of formula $CH_3(CHOH)_{n-1}CHO$ are reacted in the presence of a glyoxylate aminotransferase and a transketolase.

The principle of this process is summarized in the following reaction scheme:

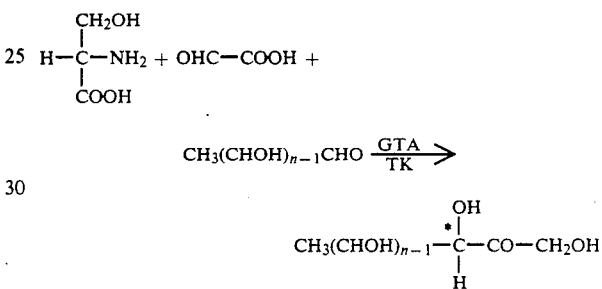

in which GTA represents a glyoxylate aminotransferase, or glyoxylate transaminase, and TK a transketolase.

The aldolization reaction is stereospecific and stereoselective; when the aldehydes contain an asymmetric carbon in the alpha-position with respect to the carbonyl, only the R isomer is converted.

L-Serine may be obtained by hydrolysis of various proteins or by fermentation using known processes; glyoxylic acid is found in immature fruits and vegetables or may be prepared by fermentation; these two starting materials can therefore be "natural".

Glyoxylate transaminase is found in all plants, and for example in oat leaves as described in Biochim. Biophys. Acta 321 p. 156-164 (1973), in beans as described in Can. J. Biochem 48 p. 486-492 (1970) or in spinach peroxisomes as described in J. Biol. Chem. 245 3821-3830 (1970).

Transketolase is present in numerous plants and in yeasts such as baker's yeast; the company Sigma markets a *Saccharomyces cerevisiae* transketolase.

According to a preferred aspect of the invention, the enzymes are extracted from spinach leaves, where they are both present in large amounts.

The reaction is carried out in an aqueous medium, preferably buffered at a pH between 7 and 8, in the presence of a transketolase coenzyme such as thiamine pyrophosphate and, better, of pyridoxal phosphate and the $Mg^{++}$ cation.

As in any enzymatic process of this type, the concentration of reactants and enzymes is determined by preliminary tests. In general, the concentration of enzymes, as measured by the activity towards their natural substrate, will be of the order of 2 to 6 units per ml, whereas that of L-serine, glyoxylic acid or the aldehyde will be 0.1M to 0.3M. The concentration of thiamine pyrophosphate will be between 0.1 µM and 2 mM, whereas pyridoxal phosphate may be introduced at a concentration of 3 µM to 2 mM, and $Mg^{++}$ at 0.2 mM to 8 mM.

The starting materials L-serine, glyoxylic acid and the aldehyde may be introduced from the start of the reaction in equimolar quantities; nevertheless, glyoxylic acid has some inhibitory effect on the reactions and it is preferable to add it to the reaction mixture in successive fractions or in a continuous manner; preferably, the concentration of this acid will not exceed 20 mM.

The process according to the invention may be used with synthetic aldehydes or those preexisting in nature or obtained by biological type processes, by hydrolysis or enzymatic reaction.

Thus acetaldehyde is obtained by enzymatic oxidation of ethanol.

2,3-Dihydroxybutyraldehyde does not exist in nature, and another subject of the invention is the process for enzymatically obtaining, from products which may be found in nature, the compound of formula II

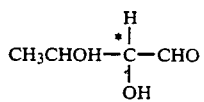

as a mixture of the 2 diastereoisomers, in which the carbon marked with an asterisk in the alpha-position with respect to the carbonyl is in the R configuration.

According to the configuration of the carbon in the β-position of the aldehyde, the formula II represents 4-deoxy-L-threose or 4-deoxy-D-erythrose; these compounds are products which are used in the preparation, according to the process of the present invention, of 6-deoxy-L-sorbose and 6-deoxy-D-fructose, respectively.

The process for the preparation of the aldehyde of formula II consist in subjecting the compound of formula III $$CH_3CHOHCOCH_2OH$$

to the action of a polyol dehydrogenase (PDH), then the resulting triol to the action of a xylose reductase (XR), according to the reaction scheme

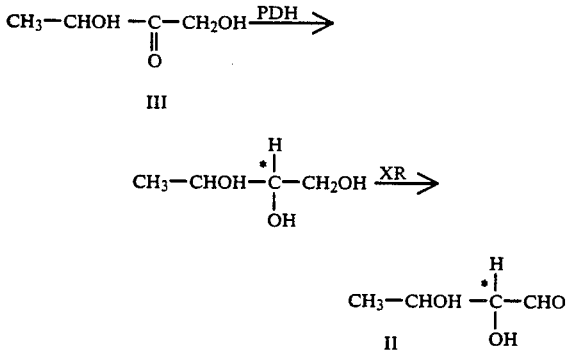

The first reaction is stereospecific, and the asymmetric carbon which appears is in the R configuration.

When the compound of formula III is prepared by the process according to the invention, from L-serine, glyoxylic acid and acetaldehyde in the presence of GTA and TK, it is in the form of a single stereoisomer, 4-deoxy-L-erythrulose, and the compound II obtained is 4-deoxy-L-threose, of formula

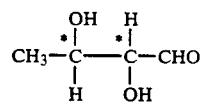

The 2 stages of the process are advantageously carried out simultaneously, introducing into the reaction mixture either a mixture of the 2 isolated enzymes or a microorganism containing the 2 enzymes.

When the 2 stages are carried out successively, NADH should be introduced into the reaction mixture in the first stage, and NAD in the second, with a system for regenerating the cofactor; when the 2 stages are carried out simultaneously, it is enough to introduce an adequate amount of NADH into the mixture; finally, in the presence of a microorganism, it is unnecessary to introduce either of these cofactors.

The enzymes are known.

Among suitable polyol dehydrogenases, the polyol dehydrogenase extracted from *Candida utilis*, marketed by Sigma, or the sorbitol dehydrogenase extracted from sheep liver, marketed by Sigma, and glycerol dehydrogenase can be mentioned.

The latter may be extracted from *Bacillus megaterium*, Cellulomonas species, *Enterobacter aerogenes* and *Aspergillus niger*; it is also marketed by the company Sigma.

It is known that xylose reductase may be extracted from *Enterobacter liquefaciens* (or *Serratia liquefaciens*) as described in Agr. Biol. Chem. 40(8) p. 1493-1503 (1976) or from Corynebacterium species as described in Agr. Biol. Chem. 40(8) p. 1485-1491 (1976).

It has been observed that the two enzymes are present in various bacteria, in particular in *Serratia liquefaciens* and *Corynebacterium equi*, or in yeasts, in particular *Rhodotorula glutinis*, *Candida utilisis* or *albicans*, or in fungi, in particular Aspergillus or Penicillium species, and it is preferable to carry out the two stages of the process simultaneously, by putting the racemic compound of formula III or one of its enantiomers in the presence of whole microorganisms or of enzymatic extracts of the latter prepared conventionally by mechanically breaking the cell walls by grinding and sonication or by enzymatic hydrolysis as described in Current Microbiology 8, p. 383-88 (1982) and in J. General Microbiology 135, p. 1391-1394 (1989).

The reactions are carried out in an aqueous medium, preferably at a pH between 7 and 8 for the first stage, and at a pH between 8.5 and 10 for the second stage or when the 2 stages are simultaneous.

The presence in the reaction medium of compounds known to increase the efficiency of the enzymes is desirable and particularly that, in the case of xylose reductase, of the $Mg^{++}$ cation at a concentration between 0.5 mM and 10 mM. The concentrations of the starting materials and the enzymes are determined by preliminary tests. They will, for example, be of the order of 0.05M to 0.3M for the materials and of 2 to 6 units/ml for the enzymes.

Another subject of the invention is the process for the enzymatic preparation of 6-deoxy-L-sorbose from naturally occurring products, which consists in subjecting the aldehyde

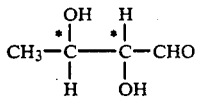

obtained by natural means, to the action of hydroxypyruvic acid, obtained by natural means, in the presence of a transketolase.

The aldehyde may be prepared, according to the process of the invention, by the action of a polyol dehydrogenase and a xylose reductase on the corresponding ketone

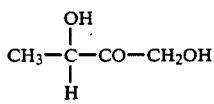

obtained by reacting L-serine, glyoxylic acid and acetaldehyde, all of natural origin, in the presence of a glyoxylate aminotransferase and a transketolase.

Hydroxypyruvic acid may be prepared by the action of L-serine on glyoxylic acid in the presence of a glyoxylate aminotransferase.

In what follows, examples of implementation of the process of the invention, applied to the preparation of 4-deoxy-L-erythrulose from acetaldehyde, of 6-deoxy-2-hexulose from racemic 2,3-dihydroxybutyraldehyde and of 6-deoxy-L-sorbose by natural means, as well as an example of the enzymatic process for the preparation of the compound of formula II, are described. A method for obtaining the two enzymes glyoxylate transaminase and transketolase from spinach leaves and a method for extracting the enzymes from *Serratia liquefaciens* and *Corynebacterium equi* are mentioned.

PREPARATION OF THE SPINACH ENZYMES

The extraction, purification and centrifugations are performed at 0° C. The centrifugations are at 10,000 g.

A) Transketolase extract:

300 g of fresh spinach leaves are finely ground in the presence of 500 ml of $K_2HPO_4$ 0.01M phosphate buffer, the pH of which is 9. The plant scraps are removed by a centrifugation followed by a filtration. 89.5 g of $(NH_4)_2SO_4$ are next added to the filtrate, and the precipitate formed is removed by centrifugation. After adding 70 g of $(NH_4)_2SO_4$ to the supernatant separated from the centrifugation residue, the suspension formed is centrifuged. The residue is isolated and will be used to prepare the glyoxylate aminotransferase. The supernatant is treated again with 36 g of $(NH_4)_2SO_4$ and centrifuged again. The centrifugation residue contains the transketolase. It is suspended in 10 ml of distilled water, then chromatographed on a Sephadex ® G-75 column 2.5 cm in diameter and 30 cm in height, eluting with distilled water. The eluate is collected in fractions of 20 ml; the quantity of transketolase contained in each of them is determined as follows:

20 μl of eluate containing the transketolase are introduced, at 25° C., into 1 ml of 0.1M glycylglycine-buffered aqueous solution at pH 7.5 containing D-xylulose 5-phosphate (9 mM), D-ribose 5-phosphate (15 mM), thiamine pyrophosphate (1.5 mM), $MgCl_2$ (8 mM) and NADH (0.42 mM) as well as one unit of triosephosphate isomerase and 10 units of glycerophosphate dehydrogenase, marketed by Sigma; one unit of triosephosphate isomerase converts 1 μmol of D-glyceraldehyde 3-phosphate, at pH 7.6 and 25° C., in 1 minute, whereas one unit of glycerophosphate dehydrogenase converts 1 μmol of dihydroxyacetone phosphate, at pH 7.4 and 25° C., in 1 minute.

The optical density of the sample is measured at 340 nm every minute; it is proportional to the concentration of NADH present. The slope, sOD, of the line representing the variation of the optical density as a function of time is then determined and the number of units per ml of the extract (U/ml) is calculated using the following equation:

$$U/ml = \frac{sOD \times V\text{sample}}{6.22 \times V\text{eluate}}$$

B) Glyoxylate aminotransferase extract

The previously isolated residue is washed with 400 ml acetone at −40° C. A powder is thus obtained which is added to 400 ml of phosphate buffer ($K_2HPO_4$, 0.01M), pH 9, and the insoluble proteins are removed by centrifugation. Three successive precipitations are next performed by adding 50 g of $(NH_4)_2SO_4$ to the centrifugation supernatants. The final centrifugation residue is recovered and chromatographed on a Sephadex ® column, as in the preparation of transketolase.

The quantity of glyoxylate aminotransferase contained in each eluate fraction is determined as follows: 5 μl of extract are introduced at 25° C. into 1 ml of 0.1M glycylglycine buffer at pH 7.6, containing L-serine (20 mM), glyoxylic acid (1.35 mM), pyridoxal phosphate (0.37 mM), NADH (0.42 mM) and 0.1 unit of glyoxylate reductase marketed by Sigma; one unit of glyoxylate reductase converts, at 25° C., 1 μmol of hydroxypyruvate to D-glycerate per minute.

The optical density of the sample is measured every minute at 340 nm and the number of units/ml of extract is determined using the same formula as in A).

PREPARATION OF THE BACTERIAL ENZYMATIC EXTRACTS

A) from *Serratia liquefaciens*:

5.25 g of cells of the strain deposited at the Institute for Fermentation, Osaka (Japan) under No. CIP 103328T are suspended in 75 ml of Tris buffer, pH 7.5, containing 0.05% (w/v) mercaptoethanol; the mixture is sonicated at the temperature of ice for 5 minutes at 200 watts, then centrifuged for 20 minutes at 4° C. at the speed of 11,000 revolutions per minute. The supernatant is recovered.

B) from *Corynebacterium equi*:

$10^6$ units of penicillin G are added to 100 ml of cell culture of the strain deposited in the Collection de Microorganismes (Culture Collection) of the Pasteur Institute, Paris (France) under the reference IFO 3730, at the end of the exponential phase, in order to make the cell walls fragile. The mixture is centrifuged after 4 hours and the residue added to 20 ml of Tris buffer (30 mM, pH=7.5) with 300 mg of lysozyme, 50 units of mutanolysin and ethylenediaminetetraacetic acid (EDTA) at a concentration of 50 mM. After 12 hours at 37° C. the medium is centrifugated at 11.000 revolutions/min. during 20 minutes and the supernatant is recovered.

The specific activities of the enzymes contained in the extracts are determined in the case of PDH by measuring the conversion of L-erythrulose (50 mM) to L-threitol or of 1,3-dihydroxy-2-butanone (50 mM) to 4-deoxy-L-threose in the presence of NADH (10 mg/ml) in Tris buffer (pH=7.5), and in the case of XR by measuring the conversion of erythritol (100 mM) to L-threose in the presence of NAD (0.2 mM) and MgCl$_2$ (2 mM) in a pH 9.7 buffer.

PREPARATION OF HYDROXYPYRUVIC ACID
(as the sodium salt)

0.476 g of Hepes buffer, 0.210 g of L-serine, 0.148 g of glyoxylic acid and 9.52 mg of pyridoxal 5-phosphate are added with stirring, at 25° C., under a nitrogen atmosphere, in the dark, to 20 ml of glyoxylate aminotransferase enzymatic extract containing 80 enzyme units. The pH of the mixture is adjusted to 7.5 by adding an N aqueous solution of NaOH.

Under these conditions, 55 mg hydroxypyruvate were formed after 5 hours, but if the reaction is continued up to 24 hours, the amount of hydroxypyruvate does not increase; in contrast, if the glyoxylate is added in fractions over the 24 hours, the yield is 65%.

In these assays the concentration of hydroxypyruvate was determined by high performance liquid chromatography on a Polypore ® column.

EXAMPLE 1

Preparation of 4-deoxy-L-erythrulose

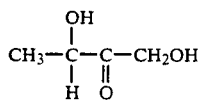

The acetaldehyde used in this reaction is obtained by enzymatic oxidation of ethanol; 0.953 g of L-serine (9 mmol), 0.017 g of MgCl$_2$, 0.055 g of thiamine pyrophosphate and 0.0318 g of pyridoxal phosphate, followed by 0.11 g of glyoxylic acid and 0.200 g of acetaldehyde, are added with stirring, at 25° C., under a nitrogen atmosphere, to 60 ml 0.1M HEPES buffer, prepared with 30 ml of transketolase extract containing 340 enzyme units, and 30 ml of glyoxylate aminotransferase extract containing 160 enzyme units; after 4 hours, 0.200 g of acetaldehyde is again added, and 0.110 g glyoxylic acid is added approximately every 4 hours. The pH is adjusted to 7.5 by adding an N aqueous solution of NaOH. After 24 hours, 160 mg of 4-deoxy-L-erythrulose are obtained, its optical rotation being:

$[\alpha_D]^{25} = 4.2$ (CH$_3$OH, C=0.059 g/l).

EXAMPLE 2

Preparation of 6-deoxy-2-hexulose

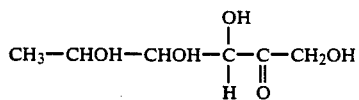

25 ml of glyoxylate aminotransferase extract containing 82 enzyme units, and 25 ml of transketolase extract containing 85 enzyme units, 0.434 g of L-serine, 0.06 g of sodium glyoxylate, 1.345 g of racemic dihydroxybutyraldehyde, 0.011 g of MgCl$_2$, 0.038 g of thiamine pyrophosphate and 0.022 g of pyridoxal phosphate are added with stirring, at 25° C., to 41 ml of 0.1M Hepes buffer; the pH is adjusted to 7.5 by adding an N aqueous solution of NaOH; 4 other 0.06 g fractions of glyoxylate are added at 7-8 hour intervals. After 48 hours, 120 ml of methanol are added to the reaction medium and the precipitated proteins are separated by centrifuging at 10,000 g for 5 minutes. The supernatant is concentrated to dryness under reduced pressure at 30° C., and the residual yellow oil, solubilized in 2 ml of water, is chromatographied on a Dowex ® 50X column, in the H+ form, 2.5 cm in diameter and 40 cm in height, eluting with distilled water. The fractions containing 6-deoxyhexulose, demonstrated by thin-layer chromatography on silica with as eluent a CHCl$_3$/CH$_3$OH (8:2-v/v) mixture, are chromatographied on a 15 g column of weakly basic Amberlite ® resin, which neutralizes them.

The solvent is removed from the eluate by distillation under reduced pressure. 378 mg of the desired product are thus obtained, which corresponds to a yield of 30.7% relatively to the dihydroxybutyraldehyde introduced. In order to characterize the final product, its diacetate was prepared by the action of acetic anhydride in pyridine (10:1-v/v) at 0° C.: 378 mg of the product are added to 12 ml of the anhydride solution, then after 24 hours, it is neutralized by adding a concentrated aqueous solution of NaHCO$_3$, and extracted with methylene chloride; the washed organic phase is diluted with one volume of toluene and the chlorinated solvent is removed under reduced pressure; the toluene solution is chromatographed on a silica column, eluting with an ethyl ether and pentane (2:1-v/v) mixture. The tetraacetates of the two expected 6-deoxy-2-hexulose diastereoisomers, namely 6-deoxy-D-fructose and 6-deoxy-L-sorbose are thus isolated from the mixture; the optical rotations of these acetates, measured at 25° C. in chloroform, are $+20°$ (C=0.039 g/l) and $-18°$ (c=0.036 g/l), respectively.

EXAMPLE 3

Preparation of the compound of formula II:

1,3-Dihydroxy-2-butanone (200 mM) and 2 g of wet Corynebacterium liquefaciens cells, which were separated from their culture medium at the end of the exponential growth phase, are added to 18 ml of Tris buffer (0.05M, pH=7.5).

After 48 hours at ambient temperature, an equilibrium state is reached; the concentration of the compound of formula II is about 40 mM, which corresponds to a yield of 20%.

EXAMPLE 4

Preparation of 6-deoxy-2-hexulose isomers: 6-deoxy-L-sorbose and 6-deoxy-D-fructose The reaction mixture containing the compound of formula II, obtained in Example 3, is centrifuged and 15 ml of transketolase extract (120 U), followed by hydroxypyruvate (5 mM), thiamine pyrophosphate (2 mM) and MgCl$_2$ (3 mM), are added to 15 ml of the supernatant, and the pH is adjusted to 7.5.

After 15 hours at ambient temperature, all the aldehyde was converted, and after treating the reaction mixture as in Example 2, 6-deoxy-2-huxulose isomers were obtained, in a proportion of 3 g/l of mixture.

EXAMPLE 5

Preparation of 6-deoxy-L-sorbose 120 units of transketolase, 2 g of Corynebacterium cells, 4-deoxy-L-erythrulose (100 mM), hydroxypyruvate (100 mM), MgCl$_2$ (2 mM) and thiamine pyrophosphate (3 mM) are added to 20 ml of Tris buffer (0.05M,

We claim:

1. A process for the preparation of a compound of formula $$CH_3(CHOH)_{n-1}-\overset{OH}{\underset{H}{\overset{*|}{C}}}-CO-CH_2OH$$

in which n is an integer from 1 to 4 and the carbon marked with an asterisk is in the S configuration, wherein L-serine, glyoxylic acid and an aldehyde of formula $CH_3(CHOH)_{n-1}CHO$ are reacted in the presence of a glyoxylate aminotransferase and a transketolase;

2. The process as claimed in claim 1, wherein the reaction medium contains thiamine pyrophosphate.

3. The process as claimed in claim 1, wherein the reaction medium contains pyridoxal phosphate and $Mg^{++}$.

4. The process as claimed in claim 1, wherein the reaction medium contains thiamine pyrophosphate, pyridoxal phosphate and $Mg^{2+}$.

5. The process as claimed in claim 1, wherein the enzymes are extracted from spinach leaves.

6. The process as claimed in claim 1, wherein the enzymes are extracted from spinach leaves and the reaction medium contains thiamine pyrophosphate, pyridoxal phosphate and $Mg^{2+}$.

7. The process as claimed in claim 1, wherein glyoxylic acid is added to the reaction mixture as fractions.

8. The process as claimed in claim 1, wherein the enzymes are extracted from spinach leaves and the reaction medium contains thiamine pyrophosphate, pyridoxal phosphate and $Mg^{2+}$, and glyoxylic acid is added to the reaction mixture as fractions.

9. The process as claimed in claim 1 for the enzymatic preparation of 6-deoxy-L-sorbose, wherein the aldehyde is made by a process wherein the ketone of the formula $$CH_3-\overset{OH}{\underset{H}{\overset{*|}{C}}}-COCH_2OH$$

is subjected to the action of a polyol dehydrogenase and then of a xylose reductase in order to obtain the aldehyde of the formula $$CH_3-\overset{OH}{\underset{H}{\overset{*|}{C}}}-\overset{H}{\underset{OH}{\overset{*|}{C}}}-CHO$$

10. The process as claimed in claim 9, wherein the aldehyde is obtained with enzymes extracted from a microorganism selected from *Serratia liquefaciens* and *Corynebacterium equi* in the presence of NADH.

11. The process as claimed in claim 9, wherein the aldehyde is obtained with enzymes extracted from a microorganism selected from *Serratia liquefaciens* and *Corynebacterium equi* in the presence of NADH and hydroxy pyruvic acid is obtained by reaction of L-serine on glyoxylic acid in the presence of glyoxalate aminotransferase.

12. The process as claimed in claim 9 wherein the enzymes are added to the reaction mixture in their microorganisms of origin, selected from *Serratia liquefaciens* and *Corynebacterium equi*.

13. The process as claimed in claim 9 wherein the enzymes are added to the reaction mixture in their microorganisms of origin, selected from *Serratia liquefaciens* and *Corynebacterium equi* and hydropyruvic acid is obtained by reacting L-serine on glyoxylic acid in the presence of glyoxalate transaminase.

14. The process as claimed in claim 9 wherein the enzymes are added to the reaction mixture in their microorganisms of origin, selected from *Serratia liquefaciens* and *Corynebacterium equi* and hydropyruvic acid is obtained by reacting L-serine on glyoxylic acid in the presence of glyoxalate transaminase extracted from spinach leaves.

* * * * *